(12) United States Patent
Yanagisawa

(10) Patent No.: US 6,777,474 B2
(45) Date of Patent: Aug. 17, 2004

(54) PREPARATION OF SULFIDE CHAIN-BEARING ORGANOSILICON COMPOUNDS

(75) Inventor: Hideyoshi Yanagisawa, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 129 days.

(21) Appl. No.: 10/201,252

(22) Filed: Jul. 24, 2002

(65) Prior Publication Data

US 2003/0027966 A1 Feb. 6, 2003

(30) Foreign Application Priority Data

Jul. 25, 2001 (JP) ........................................ 2001-224450

(51) Int. Cl.$^7$ ................................................ C08K 5/06
(52) U.S. Cl. ........................ 524/366; 524/379; 556/427
(58) Field of Search .......................... 556/427; 524/366, 524/379

(56) References Cited

U.S. PATENT DOCUMENTS

| | | | |
|---|---|---|---|
| 5,663,395 A | | 9/1997 | Gobel et al. |
| 5,859,275 A | | 1/1999 | Münzenberg et al. |
| 5,965,760 A | * | 10/1999 | Michel et al. ............... 556/427 |
| 6,015,870 A | | 1/2000 | Ichinohe et al. |
| 6,423,859 B1 | * | 7/2002 | Alig et al. .................. 556/427 |
| 6,452,034 B2 | * | 9/2002 | Cruse ......................... 556/427 |

FOREIGN PATENT DOCUMENTS

| | | |
|---|---|---|
| EP | 0 848 006 A2 | 6/1998 |
| EP | 0 908 463 A2 | 4/1999 |
| EP | 0 937 732 A2 | 8/1999 |

* cited by examiner

Primary Examiner—Robert Dawson
Assistant Examiner—Marc S. Zimmer
(74) Attorney, Agent, or Firm—Birch, Stewart, Kolasch & Birch, LLP

(57) ABSTRACT

By reacting a sulfide chain-bearing organosilicon compound having the formula:

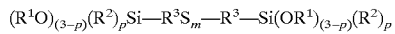

wherein $R^1$ and $R^2$ each are a monovalent $C_{1-4}$ hydrocarbon group, $R^3$ is a divalent $C_{1-10}$ hydrocarbon group, $2<m\leq 6$, and p is 0, 1 or 2, an alkali or alkaline earth metal, a halogenoalkyl group-bearing organosilicon compound having the formula:

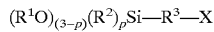

wherein X is halogen, and optionally, sulfur, a sulfide chain-bearing organosilicon compound having the formula:

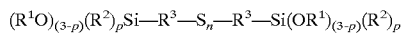

wherein $2\leq n<6$, and m>n, that is, having a shorter sulfide chain can be prepared in high yields and at a lost cost.

3 Claims, No Drawings

PREPARATION OF SULFIDE CHAIN-BEARING ORGANOSILICON COMPOUNDS

This invention relates to a method for changing the sulfide chain distribution of a sulfide chain-bearing organosilicon compound having the following general formula (1):

$$(R^1O)_{(3-p)}(R^2)_p Si-R^3-S_m-R^3-Si(OR^1)_{(3-p)}(R^2)_p \quad (1)$$

wherein $R^1$ and $R^2$ each are a monovalent hydrocarbon group having 1 to 4 carbon atoms, $R^3$ is a divalent hydrocarbon group having 1 to 10 carbon atoms, m has an average value of $2<m\leq6$, and p is 0, 1 or 2. More particularly, it relates to a method for converting a sulfide chain-bearing organosilicon compound having the formula (1) to a sulfide chain-bearing organosilicon compound having a shorter sulfide chain.

BACKGROUND OF THE INVENTION

In silica-loaded tires, bis-triethoxysilyltetrasulfide is widely used as a coupling agent between rubber and silica. However, when mixed with rubber and silica at elevated temperatures, this compound acts to increase the viscosity of the blend, which is inconvenient to subsequent operation.

To overcome this problem, shorter chain polysulfide compounds such as bis-triethoxysilylpropyldisulfide were proposed. For example, U.S. Pat. No. 5,663,395 discloses a method for preparing disulfide silanes using NaCN. This method, however, has the problem of using the toxic compound. It would be desirable to have a substitute safe method of preparing short sulfide chain-bearing organosilicon compounds at low cost.

The inventors proposed in U.S. Pat. No. 6,015,870 a method of preparing a short sulfide chain-bearing organosilicon compound by reacting a polysulfide silane of the general formula:

$$(RO)_3SiC_3H_6S_xC_3H_6Si(OR)_3$$

wherein R is methyl or ethyl, and x is a positive number of 3 to 6 on the average, at least one dry sulfur compound: $M^1_2S$ or $M^2S$ wherein $M^1$ is an alkali metal or ammonium and $M^2$ is an alkaline earth metal or zinc, and a halogenoalkoxysilane of the general formula:

$$XC_3H_6Si(OR)_3$$

wherein X is halogen and R is methyl or ethyl. When the short sulfide chain-bearing organosilicon compound is prepared by this method, however, there can also be produced a monosulfide chain-bearing organosilicon compound, that is, an organosilicon compound having a sulfide chain which does not fully participate in the reactions with silica and rubber.

SUMMARY OF THE INVENTION

An object of the present invention is to provide a safe and economical method for preparing, from a sulfide chain-bearing organosilicon compound of the formula (1), a sulfide chain-bearing organosilicon compound having a shorter average sulfide chain and having a minimal content of monosulfide chain-bearing organosilicon compound in its composition.

The present invention provides a method for preparing a sulfide chain-bearing organosilicon compound having the following general formula (3):

$$(R^1O)_{(3-p)}(R^2)_p Si-R^3-S_n-R^3-Si(OR^1)_{(3-p)}(R^2)_p \quad (3)$$

wherein $R^1$ and $R^2$ each are a monovalent hydrocarbon group having 1 to 4 carbon atoms, $R^3$ is a divalent hydrocarbon group having 1 to 10 carbon atoms, n has an average value of $2\leq n<6$, and p is 0, 1 or 2. The method involves the step of reacting a sulfide chain-bearing organosilicon compound having the following general formula (1):

$$(R^1O)_{(3-p)}(R^2)_p Si-R^3-S_m-R^3-Si(OR^1)_{(3-p)}(R^2)_p \quad (1)$$

wherein $R^1$, $R^2$, $R^3$ and p are as defined above, and m has an average value of $2<m\leq6$ and $m>n$, an alkali metal or alkaline earth metal, a halogenoalkyl group-bearing organosilicon compound having the following general formula (2):

$$(R^1O)_{(3-p)}(R^2)_p Si-R^3-X \quad (2)$$

wherein $R^1$, $R^2$, $R^3$ and p are as defined above, and X is a halogen atom, and optionally, sulfur. With this method, the desired sulfide chain-bearing organosilicon compound, and especially a sulfide chain-bearing organosilicon compound of formula (3) wherein n has an average value of 2 to 3 and having a minimal content of monosulfide chain-bearing organosilicon compound in its composition is produced in high yields and at low cost.

DESCRIPTION OF THE PREFERRED EMBODIMENTS

Briefly stated, according to the invention, a sulfide chain-bearing organosilicon compound of formula (3) is obtained by reacting a sulfide chain-bearing organosilicon compound of formula (1), an alkali metal or alkaline earth metal, a halogenoalkyl group-bearing organosilicon compound of formula (2), and optionally, sulfur.

One starting reactant is a sulfide chain-bearing organosilicon compound having the following general formula (1).

$$(R^1O)_{(3-p)}(R^2)_p Si-R^3-S_m-R^3-Si(OR^1)_{(3-p)}(R^2)_p \quad (1)$$

In the formula, $R^1$ and $R^2$ are independently selected from monovalent hydrocarbon groups having 1 to 4 carbon atoms, for example, alkyl and alkenyl groups such as methyl, ethyl, n-propyl, i-propyl, n-butyl, i-butyl, t-butyl, allyl and methallyl. $R^3$ is selected from divalent hydrocarbon groups having 1 to 10 carbon atoms, for example, alkylene, arylene and alkenylene groups and combinations thereof, such as methylene, ethylene, propylene, n-butylene, i-butylene, hexylene, decylene, phenylene, and methylphenylethylene. The subscript m has an average value of $2<m\leq6$ and preferably $3\leq m\leq4$, and p is equal to 0, 1 or 2.

Typical examples of the compound of formula (1) are given below.

$$(CH_3O)_3Si-(CH_2)_3-S_4-(CH_2)_3-Si(OCH_3)_3$$

$$(CH_3CH_2O)_3Si-(CH_2)_3-S_4-(CH_2)_3-Si(OCH_2CH_3)_3$$

In the above-described compound, S has a distribution partially because of disproportionation reaction, so that its number is described as an average value. In formula (1), m has an average value of $2<m\leq6$ and preferably $3<m\leq4$.

Any alkali metal or alkaline earth metal may be used herein although metallic sodium or potassium is preferred.

The halogenoalkyl group-bearing organosilicon compound used herein has the following general formula (2).

$$(R^1O)_{(3-p)}(R^2)_p Si-R^3-X \quad (2)$$

In the formula, $R^1$, $R^2$, $R^3$ and p are as defined above, and X is a halogen atom such as Cl, Br or I.

Typical examples of the compound of formula (2) are given below.

(CH₃O)₃Si—(CH₂)₃—Cl (CH₃O)₃Si—(CH₂)₃—Br (CH₃CH₂O)₃Si—(CH₂)₃—Cl (CH₃CH₂O)₃Si—(CH₂)₃—Br (CH₃CH₂O)₃Si—CH₂CH(CH₃)CH₂—Cl

When the reaction is conducted, sulfur is added if desired for adjusting the length of sulfide chain. It is not preferred to add a large amount of sulfur because the resulting product contains more monosulfide chain-bearing organosilicon compound.

The use of a solvent is optional when the end compound is prepared according to the invention. A solventless system is acceptable. Examples of the solvent, if used, include aliphatic hydrocarbons such as pentane, hexane, heptane and octane, aromatic hydrocarbons such as benzene, toluene and xylene, alcohols such as methanol and ethanol, and ethers such as dibutyl ether, tetrahydrofuran and dioxane. Of these, the ethers such as dibutyl ether, tetrahydrofuran and dioxane and the alcohols such as methanol and ethanol are preferred.

The method of the invention may be carried out in any desired order. For example, once the compound of formula (1) is reacted with the alkali metal or alkaline earth metal and optionally, sulfur, the reaction product is reacted with the compound of formula (2). Alternatively, a reactor is charged with the compound of formula (1), the compound of formula (2) and optionally, sulfur, and the alkali metal or alkaline earth metal is added thereto for reaction.

The reaction temperature is not critical and generally ranges from room temperature to about 200° C., and preferably from about 60° C. to about 170° C. The reaction time is usually about 30 minutes or more. The reaction proceeds to completion within about 2 hours to about 15 hours.

For the reaction, the molar ratio of the respective reactants is preferably determined as follows. With respect to the molar ratio of the compound of formula (1) to the alkali or alkaline earth metal, the alkali or alkaline earth metal may be added in accordance with the desired value of n in formula (3). When the alkali metal is used, an equimolar amount of the compound of formula (2) is generally added. When the alkaline earth metal is used, a 2-fold molar amount of the compound of formula (2) is added. It is noted that the system becomes alkaline as the moles of the compound of formula (2) decreases, and becomes nearly neutral as the moles of the compound of formula (2) increases. More illustratively, when reaction is made among 1 mole of the compound of formula (1) wherein m has an average value of 4, 2 moles of the alkali metal and 2 moles of the compound of formula (2), there is obtained a compound of formula (3) wherein n has an average value of 2. The amount of sulfur added herein is arbitrary. For example, 0.5 mole of sulfur is added when it is desired for the average value of n to be 2.5 under the above-described molar ratios of the reactants. The amount of the solvent used is arbitrary. When the solvent is used, it may be distilled off in vacuum at the end of reaction and before or after the salt formed is separated by filtration.

The thus obtained compound has the following general formula (3).

$$(R^1O)_{(3-p)}(R^2)_p Si—R^3—S_n—R^3—Si(OR^1)_{(3-p)}(R^2)_p \quad (3)$$

In the formula, R¹ and R² each are a monovalent hydrocarbon group having 1 to 4 carbon atoms, and R³ is a divalent hydrocarbon group having 1 to 10 carbon atoms, examples of which are as illustrated in conjunction with formula (1). The subscript p is 0, 1 or 2. The subscript n has an average value of 2≦n<6, and is smaller than m in formula (1), i.e., m>n, and preferably has an average value of 2≦n≦3. In the compound (mixture) obtained by the inventive method, the content of the compound of formula (3) wherein n=1 is at most 5 mol %, and especially at most 2 mol %.

Typical examples of the compound of formula (3) are given below.

(CH₃O)₃Si—(CH₂)₃—S₂—(CH₂)₃—Si(OCH₃)₃

(CH₃O)₃Si—(CH₂)₃—S₃—(CH₂)₃—Si(OCH₃)₃

(CH₃CH₂O)₃Si—(CH₂)₃—S₂—(CH₂)₃—Si(OCH₂CH₃)₃

(CH₃CH₂O)₃Si—(CH₂)₃—S₃—(CH₂)₃—Si(OCH₂CH₃)₃

(CH₃CH₂O)₃Si—CH₂CH(CH₃)CH₂—S₃—CH₂CH(CH₃)CH₂—Si(OCH₂CH₃)₃

EXAMPLE

Examples of the invention are given below by way of illustration and not by way of limitation.

Example 1

A 1-liter separable flask equipped with a nitrogen gas inlet, thermometer, Dimroth condenser and dropping funnel was charged with 250 g of tetrahydrofuran, 269 g (0.5 mol) of bis-triethoxysilylpropyltetrasulfide (m=4), and 23 g (1.0 mol) of metallic sodium. Reaction was conducted at 60° C. for 4 hours. Thereafter, 240.5 g (1.0 mol) of 3-chloropropyl-triethoxysilane was added dropwise over 30 minutes. After the completion of dropwise addition, the reaction solution was ripened for 8 hours. The solution was filtered. The filtrate was concentrated in vacuum in a rotary evaporator, yielding 398 g of a brown clear liquid. On analysis by infrared (IR) absorption spectroscopy and proton nuclear magnetic resonance (¹H-NMR) spectroscopy, it was confirmed to be a sulfide group-bearing alkoxysilane of the following average compositional formula.

(CH₃CH₂O)₃Si(CH₂)₃—S₂—(CH₂)₃Si(OCH₂CH₃)₃

To confirm the sulfide group distribution of the compound, supercritical chromatography was carried out. Its sulfide silane distribution (mol %) is shown below.

| | |
|---|---|
| n = 1 | 1% |
| n = 2 | 95% |
| n = 3 | 3% |
| n = 4 | 1% |
| n = 5 | ≦0.1% |

The bis-triethoxysilylpropyltetrasulfide used as the starting reactant had the sulfide silane distribution (mol %) shown below.

| | |
|---|---|
| n = 1 | 0.1% |
| n = 2 | 18% |
| n = 3 | 30% |
| n = 4 | 25% |
| n = 5 | 17% |

|  |  |
|---|---|
| n = 6 | 6% |
| n = 7 | 3% |
| n = 8 | 1% |

Example 2

Reactions were conducted as in Example 1 except that 6.4 g (0.2 mol) of sulfur was added during the reaction with metallic sodium. There was obtained 397 g of a brown clear liquid. On analysis by IR and $^1$H-NMR spectroscopy, it was confirmed to be a sulfide group-bearing alkoxysilane of the following average compositional formula.

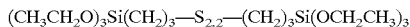

$(CH_3CH_2O)_3Si(CH_2)_3—S_{2.2}—(CH_2)_3Si(OCH_2CH_3)_3$

To confirm the sulfide group distribution of the compound, supercritical chromatography was carried out. Its sulfide silane distribution (mol %) is shown below.

|  |  |
|---|---|
| n = 1 | 1% |
| n = 2 | 79% |
| n = 3 | 16% |
| n = 4 | 3% |
| n = 5 | 1% |
| n = 6 | ≦0.1% |

Comparative Example 1

A 1-liter separable flask equipped with a nitrogen gas inlet, thermometer, Dimroth condenser and dropping funnel was charged with 250 g of ethanol, 74.0 g (0.14 mol) of bis-triethoxysilylpropyltetrasulfide (m=4), 15.6 g (0.2 mol) of dry sodium sulfide, and 0.75 g (0.02 mol) of sulfur. Reaction was conducted at 80° C. for 1 hour. Thereafter, 96.2 g (0.4 mol) of 3-chloropropyltriethoxysilane was added dropwise over 20 minutes. After the completion of dropwise addition, the reaction solution was ripened for 8 hours. The solution was filtered. The filtrate was concentrated in vacuum in a rotary evaporator, yielding 138 g of a brown clear liquid. On analysis by IR and $^1$H-NMR spectroscopy, it was confirmed to be a sulfide group-bearing alkoxysilane of the following average compositional formula.

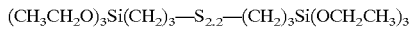

$(CH_3CH_2O)_3Si(CH_2)_3—S_{2.2}—(CH_2)_3Si(OCH_2CH_3)_3$

To confirm the sulfide group distribution of the compound, supercritical chromatography was carried out. Its sulfide silane distribution (mol %) is shown below.

|  |  |
|---|---|
| n = 1 | 5% |
| n = 2 | 75% |
| n = 3 | 14% |
| n = 4 | 5% |
| n = 5 | 1% |
| n = 6 | ≦0.1% |

According to the invention, from a sulfide chain-bearing organosilicon compound of the formula (1), a polysulfidesilane having a shorter polysulfide chain can be prepared in high yields and at a lost cost. The resulting compound is of a composition having a low content of monosulfide chain-bearing organosilicon compound which is less reactive with rubber. The method is valuable in the industry.

Japanese Patent Application No. 2001-224450 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing a sulfide chain-bearing organosilicon compound having the following general formula (3):

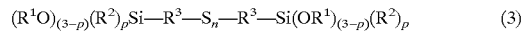

$(R^1O)_{(3-p)}(R^2)_pSi—R^3—S_n—R^3—Si(OR^1)_{(3-p)}(R^2)_p$ (3)

wherein $R^1$ and $R^2$ each are a monovalent hydrocarbon group having 1 to 4 carbon atoms, $R^3$ is a divalent hydrocarbon group having 1 to 10 carbon atoms, n has an average value of 2≦n<6, and p is 0, 1 or 2, said method comprising the step of reacting a sulfide chain-bearing organosilicon compound having the following general formula (1):

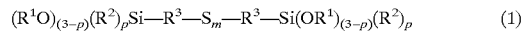

$(R^1O)_{(3-p)}(R^2)_pSi—R^3—S_m—R^3—Si(OR^1)_{(3-p)}(R^2)_p$ (1)

wherein $R^1$, $R^2$, $R^3$ and p are as defined above, and m has an average value of 2<m≦6 and m>n, an alkali metal or alkaline earth metal, a halogenoalkyl group-bearing organosilicon compound having the following general formula (2):

$(R^1O)_{(3-p)}(R^2)_pSi—R^3—X$ (2)

wherein $R^1$, $R^2$, $R^3$ and p are as defined above, and X is a halogen atom, and optionally, sulfur.

2. The method of claim 1 wherein a sulfide chain-bearing organosilicon compound having the formula (3) wherein n has an average value of 2 to 3 is obtained using a sulfide chain-bearing organosilicon compound having the formula (1) wherein m has an average value of 3 to 4.

3. The method of claim 1 wherein the reaction is conducted in a solvent selected from the group consisting of alcohols and ethers.

* * * * *